(12) United States Patent
Kerrod et al.

(10) Patent No.: US 7,628,955 B2
(45) Date of Patent: Dec. 8, 2009

(54) CENTRIFUGATION DEVICE

(75) Inventors: Ian Kerrod, Hawarden (GB); Peter Lomas, Wirral (GB)

(73) Assignee: Thermo Shandon Limited (GB)

( * ) Notice: Subject to any disclaimer, the term of this patent is extended or adjusted under 35 U.S.C. 154(b) by 562 days.

(21) Appl. No.: 10/542,257

(22) PCT Filed: Aug. 13, 2003

(86) PCT No.: PCT/GB03/03524

§ 371 (c)(1),
(2), (4) Date: Dec. 8, 2005

(87) PCT Pub. No.: WO2004/063721

PCT Pub. Date: Jul. 29, 2004

(65) Prior Publication Data

US 2006/0135337 A1     Jun. 22, 2006

(30) Foreign Application Priority Data

Jan. 16, 2003   (GB) ................................. 0301047.7

(51) Int. Cl.
*G01N 9/30* (2006.01)
(52) U.S. Cl. .......................... 422/72; 422/102; 422/104; 436/177; 436/180
(58) Field of Classification Search ................. 422/72, 422/102, 104; 436/177, 180
See application file for complete search history.

(56) References Cited

U.S. PATENT DOCUMENTS

| | | | |
|---|---|---|---|
| 3,676,387 A | * | 7/1972 | Lindlof ........................ 524/489 |
| 4,696,743 A | | 9/1987 | Billington |
| 4,853,188 A | | 8/1989 | Matsumi |
| 4,874,582 A | | 10/1989 | Billington |
| 5,679,154 A | * | 10/1997 | Kelley et al. .................. 118/52 |
| 6,162,401 A | | 12/2000 | Callaghan |

FOREIGN PATENT DOCUMENTS

EP          0 184 374       6/1986

\* cited by examiner

*Primary Examiner*—Lyle A Alexander
*Assistant Examiner*—Dennis M White
(74) *Attorney, Agent, or Firm*—Thomas A. Runk; Fulwider Patton LLP

(57) ABSTRACT

A centrifugation device comprising a combined sample chamber and slide holder adapted to be mounted, with a microscope slide (26), in a centrifuge in a predetermined position, after placing a fluid biological sample containing cells in the sample chamber. The device comprises an integrally moulded body (10) affording a base (14) which engages the microscope slide, and also affording a back plate (14) connected with the base plate by an integral hinge (22) a latch mechanism formed integrally with the remainder of the device is arranged, when the back plate (14) is closed against the rear of a microscope slide (26) engaged with the base (14), to locate the slide between the base and the back plate and to hold the back plate in this closed position until fracture of a retaining element from the integrally moulded body. Thus the device can be used once only. The base includes an aperture communicating with the sample chamber and carries an elastomeric gasket (26) for sealing the edges of the aperture with respect to the surface of the microscope slide. The material of the gasket (20) includes an oil component which, in use, forms an oil film on the microscope slide where the gasket contacts the slide, which can act as a barrier to aqueous fluid and prevents migration of such fluid past the region of the slide contacted by the gasket.

8 Claims, 6 Drawing Sheets

CENTRIFUGATION DEVICE

RELATED APPLICATIONS

This is a U.S. national phase of PCT/GB2003/003524 filed 13 Aug. 2003, claiming priority from GB 0301047.7 filed Jan. 16, 2003.

BACKGROUND

THIS INVENTION relates to a centrifugation device comprising a combined sample chamber and slide holder adapted to be mounted, with a microscope slide, in a centrifuge in a predetermined position, after placing, in the sample chamber, a fluid biological sample containing cells, the device being so-arranged that when the centrifuge is operated, a thin layer—ideally a monolayer of cells is deposited from the fluid onto a predetermined deposition area on the glass microscope slide. Such a centrifugation device is herein referred to as being "of the kind specified".

Various forms of centrifugation device of the kind specified have been known in the past. Examples of such devices are disclosed, for example, in U.S. Pat. Nos. 4,391,710; 4,696,743; 4,853,188 and 4,874,582 and European Patents Nos. 0184374 and 0047840. Some examples have been reusable, that is to say it was possible and intended that after the device had been used to deposit cells from a fluid sample onto a first microscope slide, and the slide removed, the device could be cleaned, a fresh slide fitted, a fresh fluid sample placed in the sample chamber and the device again placed into the centrifuge and so on indefinitely. In these arrangements the slide is, of course retained by a releasable and re-attachable clip of some description. Some later centrifugation devices of the kind specified were of the single-use type, that is to say they were designed in such a way that they could not, or could not conveniently, be used more than once, thereby avoiding contamination problems resulting from improper cleaning procedures between uses. In view of their inevitably disposable nature, devices of the latter character have generally been largely of plastics in order to minimise production costs.

SUMMARY OF THE INVENTION

It is an object of the present invention to provide an improved centrifugation device of the single use type.

According to one aspect of the present invention there is provided a centrifugation device as herein defined comprising an integrally moulded body affording a base adapted for engagement with a microscope slide, structure on one side of the base defining a chamber for a fluid sample, with an opening for the introduction of fluid to said chamber, the base including an aperture and carrying a means for sealing the edges of such aperture with respect to the surface of a microscope slide placed across the base, or for allowing the passage of liquid but obstructing the passage of cells, the centrifugation device further including a back plate connected with the base plate by an integral hinge and a latch mechanism formed integrally with the remainder of the device and arranged, when the back plate is closed against the rear of a microscope slide engaged with the base, to locate the slide between the base and the cover plate and to hold the cover plate in this closed position until fracture of a retaining element from the integrally moulded body.

The catch arrangement preferably comprises a detent carried by the back plate adjacent the free edge of the latter and which, in operation, co-operates, in the closed position of the device, with a complementary latch carried by the body of the device and connected with said body by an integral live hinge, the catch arrangement further comprising a shield element which, in the condition of the device before use, is secured in a position in which it extends over the complementary latch at a predetermined distance from the integral live hinge of the said complementary latch, the arrangement being such that in the closed position, with the shield element still attached, the detent on the back plate is retained between the shield element and the complementary latch and the shield element counteracts a turning moment applied to the complementary latch as a result of tension in the back plate detent, whilst on breaking of a frangible retaining element holding the shield member in position relative to the device body, the shield element is able to move away from said complementary latch allowing the latter to swing away from the back plate detent for release of the back plate detent to allow the back plate to swing away from the body of the device, and to allow removal of the microscope slide.

The complementary latch may be provided with a retaining arm which engages a face of the detent on the back plate to push the detent across the abutment face of the latch as the latch tilts outwardly and backwards during the release of the detent after rupture of the connection of the shield member with the body part, and thus to ensure release of the detent from the latch.

BRIEF DESCRIPTION OF THE DRAWINGS

An embodiment of the invention is described below by way of example with reference to the accompanying drawings in which.

DETAILED DESCRIPTION OF THE PREFERRED EMBODIMENTS

Figure 1:
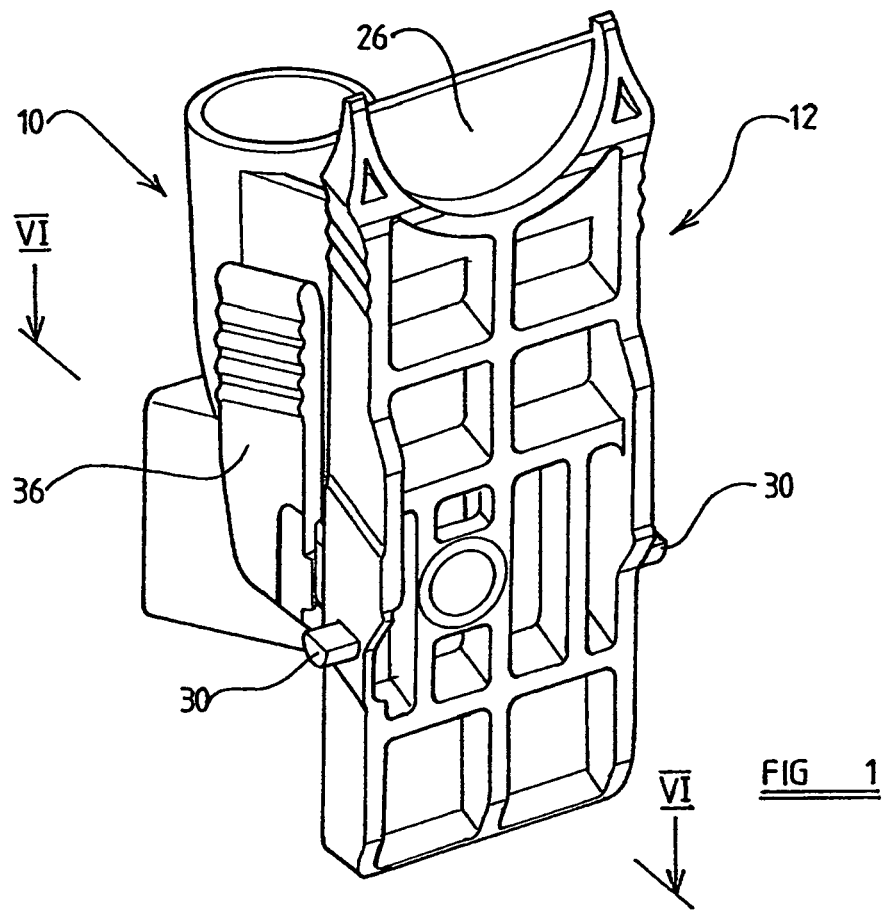
FIG. 1 is a perspective view, from the rear and above, of a centrifugation device in accordance with the invention in the condition in which a back plate is closed against a body part with a microscope slide located therebetween.
Figure 2:
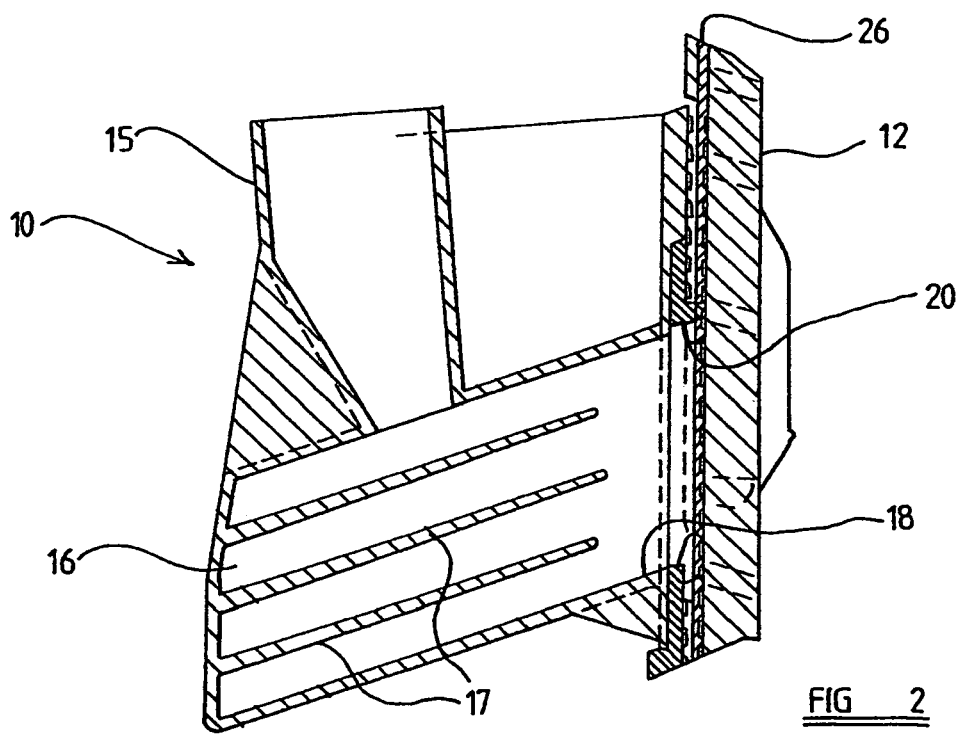
FIG. 2 is a view in vertical section through the device and microscope slide of FIG. 1.
Figure 3:
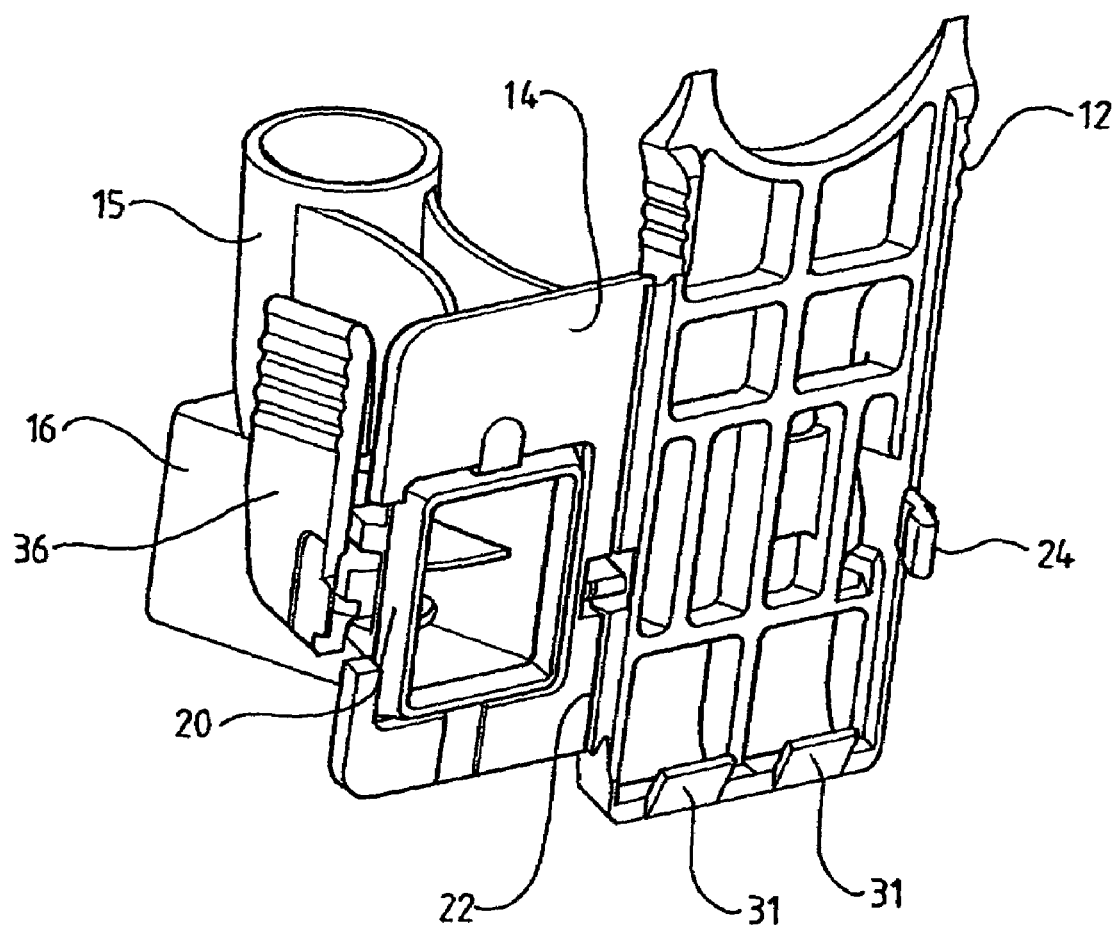
FIG. 3 is a perspective view corresponding to FIG. 1 but showing the device with the back plate in an open position in relation to the body part, without the microscope slide.
Figure 4:
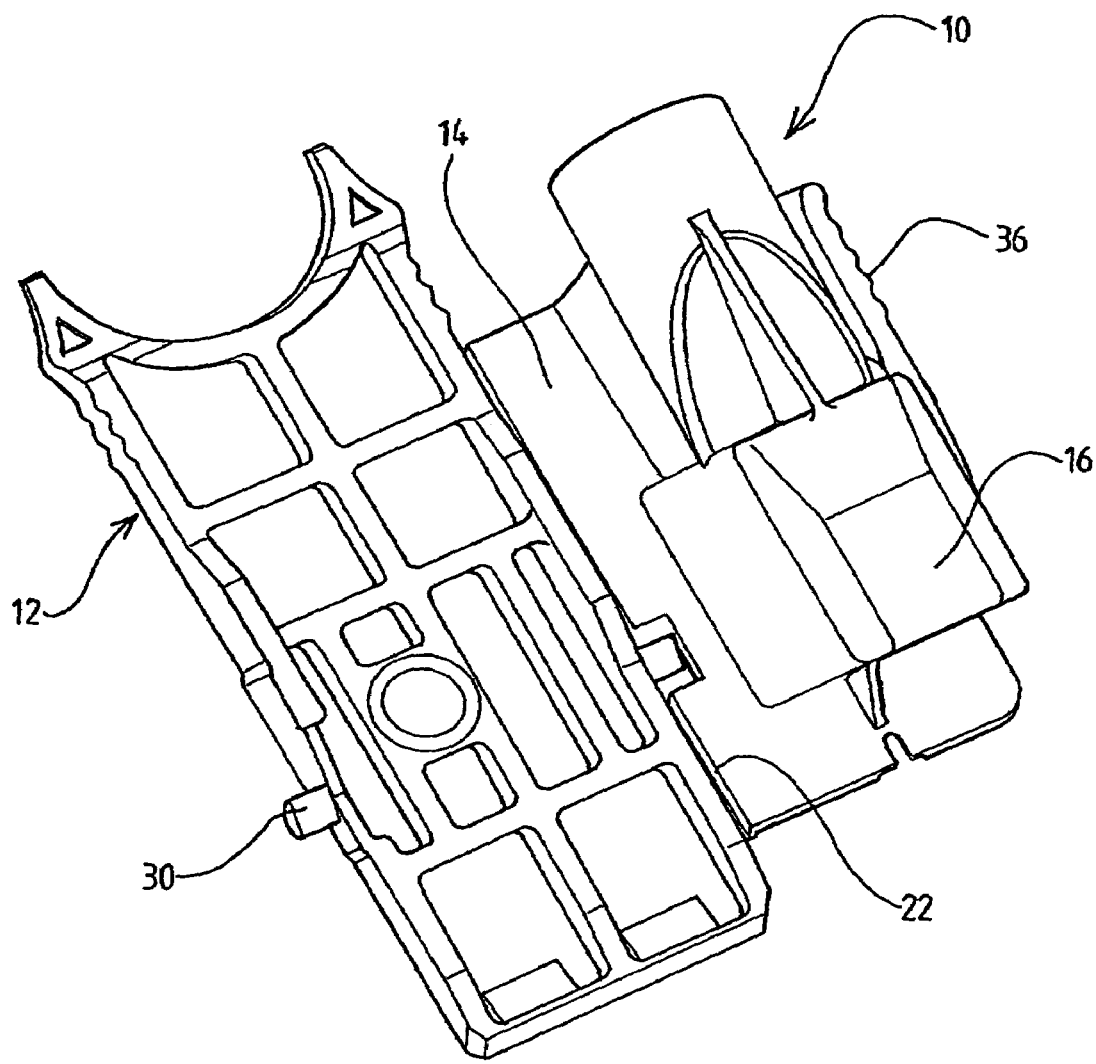
FIG. 4 is a perspective view corresponding to FIG. 3 but from the front and below.
Figure 5:
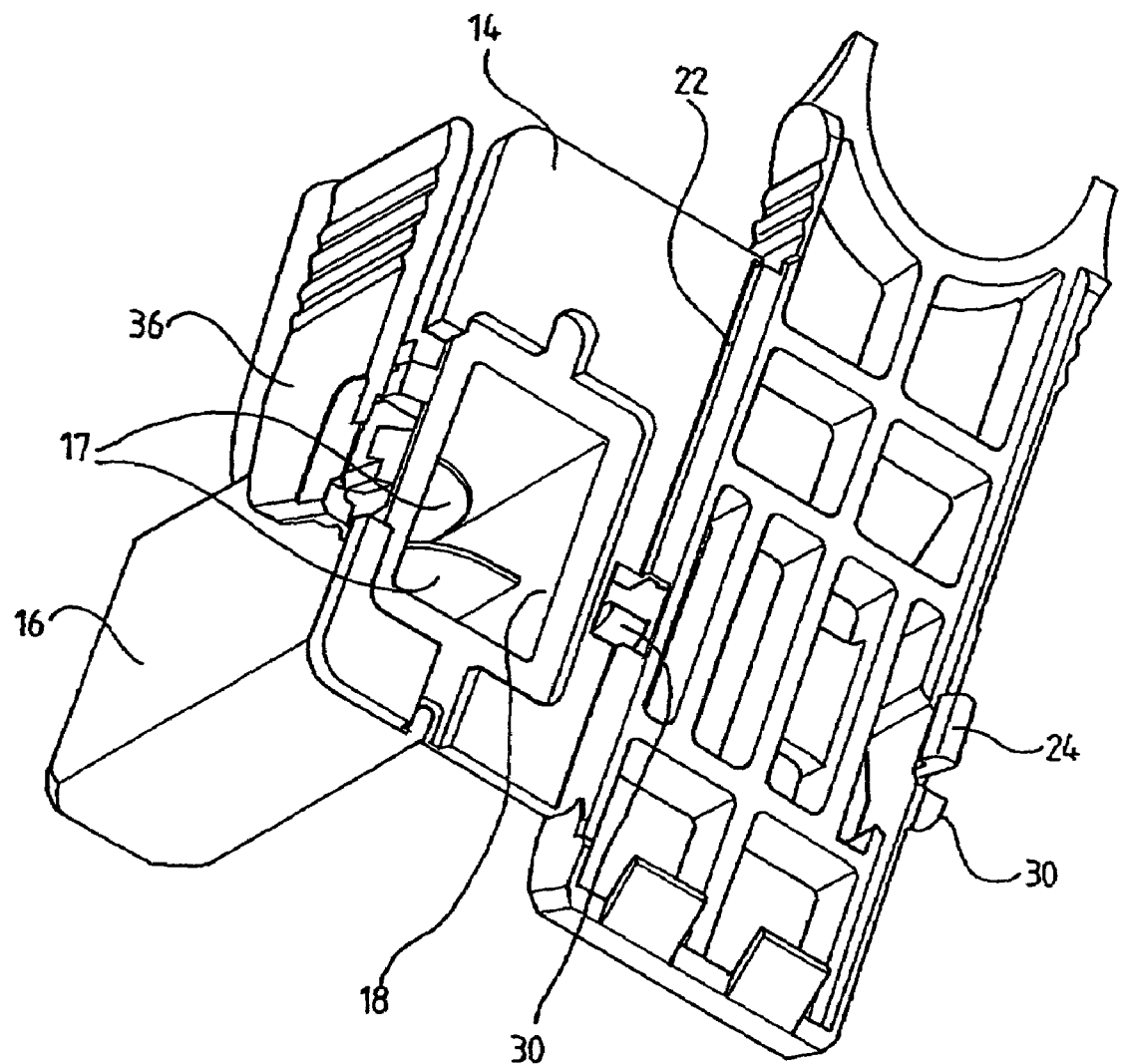
FIG. 5 is a perspective view from the rear and below of the device with the back late in an open position with respect to the body part of the device.

Referring to FIGS. 1 to 4, a centrifugation device in accordance with the present invention comprises a body part 10 and a back plate 12 formed integrally with one another by moulding in a suitable plastics material such as polypropylene, the back plate 12 being connected with the body part 10 by way of an integral "living hinge" 22. As shown in FIGS. 3 to 5, the body part 10 comprises a generally planar base or flange 14 which carries on its front side integral structure providing a sample chamber 16 which is closed at its end remote from the base 14 and which terminates, in the plane of the base 14, in a port 18 which, in the preferred embodiment, is rectangular. A funnel 15 extends upwardly from an entrance opening in the sample chamber, whereby a fluid sample can be introduced into the sample chamber 16. As shown in FIGS. 2 and 3, a resilient gasket, for example of an injection mouldable elastomer, referenced 20 in FIGS. 2 and 3 is carried by the base 14. The gasket 20 extends around the port 18 and protrudes slightly rearwardly from the rear face of the base 14, for sealing against the adjacent surface of glass microscope slide (26, FIG. 2). The material of the gasket 20 is preferably a thermoplastic elastomer such as Evoprene G936, and is moulded in situ on the backplate, the body 10 and integral backplate 12 and the gasket being formed by a two shot injection moulding technique, with the body 10 and backplate being formed in one shot and the gasket being formed in the other shot. The gasket incorporates an oil component which, in use, forms a thin oil film on the slide 26 where the gasket contacts the slide. This film acts as a barrier to the aqueous fluid of the biological sample and tends to prevent migration of such fluid, from the cell layer deposited on the slide, beyond the boundary defined by the region of contact of the gasket, after opening of the centrifugation device and removal of the side. Subsequent processing of the slide and sample layer generally involves immersion of the slide in an alcohol based medium which also removes the thin oil film.

The base 14 is generally rectangular, as is the back plate 12, and the living hinge 22 extends along one vertical edge of the base 14 and the adjacent vertical edge of the back plate 12. The vertical edge of the back plate 12 remote from the living hinge 22 carries a detent 24 for co-operating with elements carried by the body 10 adjacent the edge of the base 14 remote from the living hinge 22 and which elements, together with detent 24, form a catch arrangement whereby the back plate may be secured in a closed position on the base 14 with a microscope slide, indicated at 26 in FIGS. 1 and 2, held between the base 14 and the back plate 12. As illustrated in FIGS. 1 and 5, the upper edge of the back plate 12 may be scalloped or recessed, as indicated, to allow ready grasping of the upper edge of the microscope slide 26 between finger and thumb during removal of the slide from the device after centrifugation, as described below.

In use of the device, a microscope slide is located between the back plate 12 and the base 14. (FIGS. 3 and 5 show integral hooks 31 to support the lower end of a microscope slide 26 fitted against the front surface of the back plate until the back plate 12, with the slide, is closed against the base 14). In this condition, as illustrated in FIG. 2, the gasket 20 engages the adjacent surface of the slide 26 in a sealing-tight manner.

The device is then mounted in a centrifuge (not shown) in such a manner that bosses 30 projecting from the sides of the back plate act as journals received in bearings provided by complementary slots in mounting structure within the centrifuge. When the centrifuge is at rest, the device rests in the centrifuge in a position in which the slide 26 is at an angle. When the centrifuge is spun up, the device pivots about the axis of bosses 30, into a position in which the slide is vertical. When the centrifuge is spun, the centrifugal force generated produces a rapid settling of the cells within the biological sample against the surface of the glass slide 26, within an area bounded by gasket 20 and these cells remain in a thin layer on the slide after the centrifuge is stopped. In order to ensure a more even distribution of cells across the exposed area of the slide during the centrifuging step, the sample chamber has a plurality of parallel baffle plates 17 extending alternately from opposite sides of the sample chamber, part-way across the latter and generally parallel with the bottom wall of the sample chamber. After the centrifuge is stopped, the centrifugation device removed from the centrifuge, and the slide carefully removed after opening of the back plate as described below.

Figure 6:
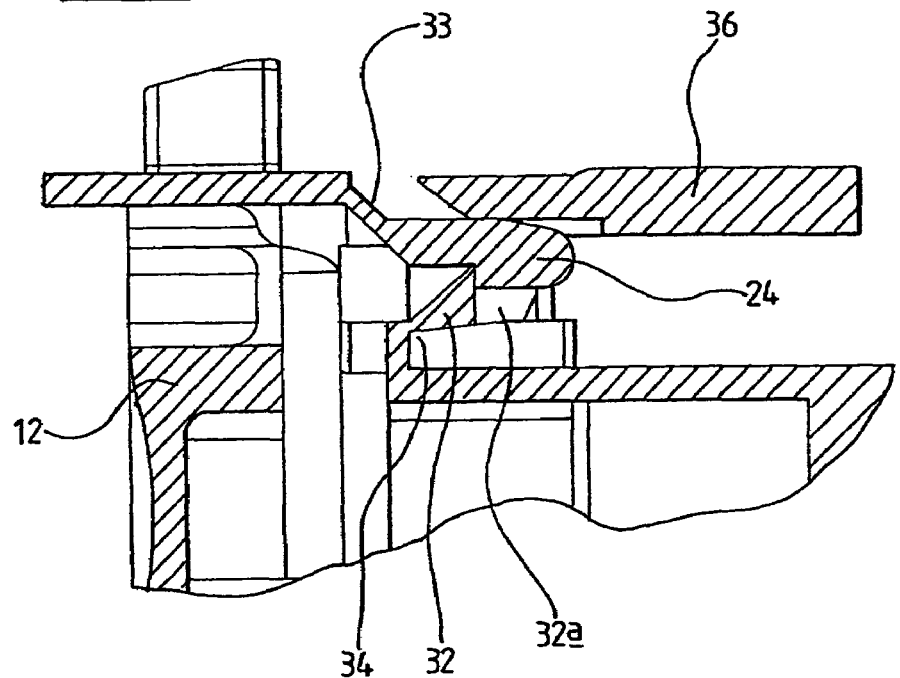
FIG. 6 is a partial view in horizontal section, and to an enlarged scale, through the device of FIGS. 1 to 4, along the line VI-VI in FIG. 1 showing details of the catch arrangement, in the closed condition of the back plate.
Figure 7:
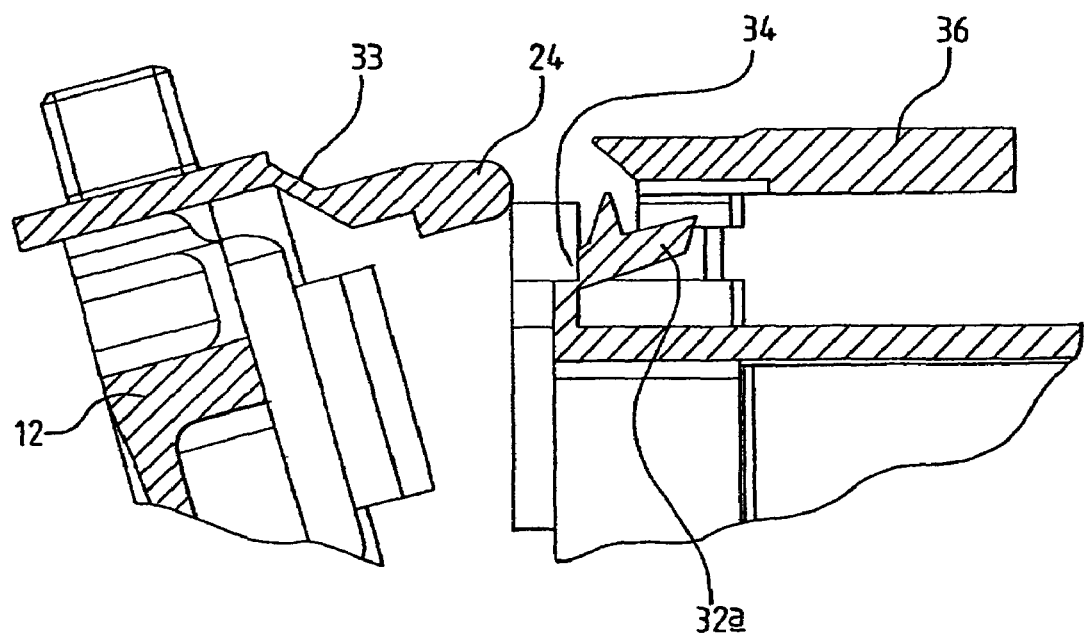
FIG. 7 is a corresponding partial section of view in the open condition of the back plate and FIG. 8 is a fragmentary rear elevation view, also to an enlarged scale, of the body part of the device showing the parts of the catch arrangement carried thereby.
Figure 8:
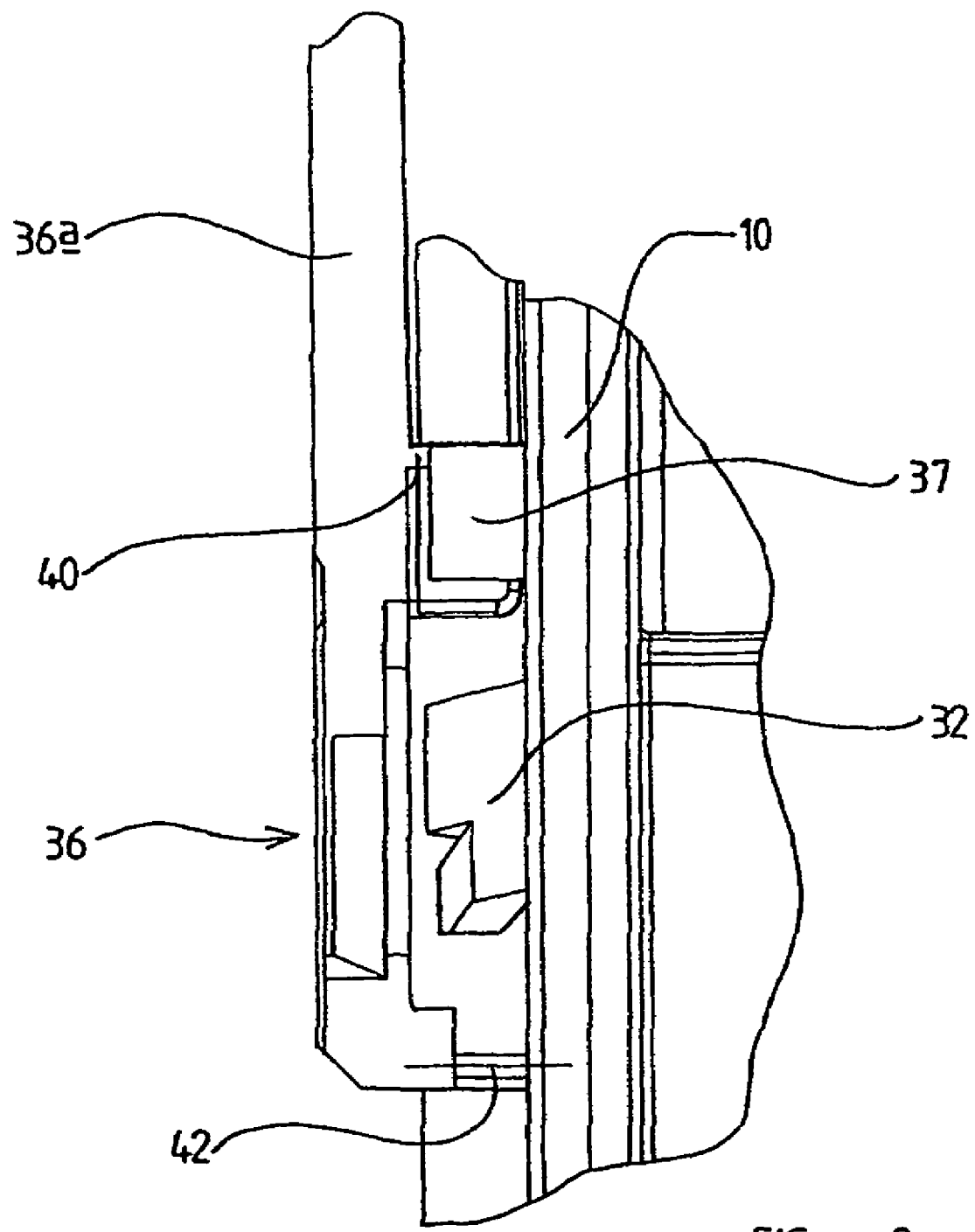

Referring to FIGS. 6, 7 and 8, the fragmentary horizontal section views of FIG. 6 and FIG. 7 show a portion of the back plate 12 adjacent the edge carrying the detent 24 and show the adjacent portion of the body 10 and a latch 32 which is connected with the remainder of the body 10 by an integral live hinge 34. The detent 24 comprises a head portion connected with the adjacent edge of the backplate 12 by a relatively flexible arm 33. The body 10 also carries an integrally formed shield element 36 in the form of a generally flat plate which is disposed at a predetermined distance from the adjoining side wall of the body 10 and extends over the latch 32. There is thus defined between the latch 32 and the shield element 36 a narrow space through which the detent 24 is projected in the closed condition of the back plate shown as FIG. 6. In this position, an abutment surface of the detent 24, facing away from the free end or nose of the detent 24 engages an opposing abutment face of the latch element 32 and, additionally, the surface of the nose of the detent facing away from the shield element 36 is engaged by an opposing surface of the latch 32, afforded by an extension 32A. When the back plate is moved from the open position shown in FIG. 7 to the closed position shown in FIG. 6, the natural resilience of the living hinge 34 causes the latch 32, originally deflected downwards by the nose of the detent 24, to spring back again into the locking position shown in FIG. 6. In this closed position, deflection of the detent 24 away from the part of the body 10 to which the hinge 34 is attached, being deflection such as would allow disengagement of the detent 24 from the latch 32, is prevented by engagement of the detent 24 with the shield element 36.

As a result of the arrangement described, it is not possible to open the back plate 12 without removal or displacement of the shield element 36 which, as described below, necessarily involves rupture of a connecting element. As indicated in FIG. 8, the shield element 36 conveniently takes the form of a lever having a free end 36A and pivotally connected with a projection 37 from the body 10 byway of an integral living hinge 40. The end of the lever 36 remote from free end 36A is secured by a narrow and hence weakened connection 42 to the side of body 10. When it is desired to release the back plate 12 for removal of the slide 26, the free end 36A of the shield element 36 is pressed manually towards the adjacent surface of the body part 10 causing the opposite end of the lever 36 to break from its connection 42 with the body part 10, allowing the portion of the element 36 overlying the detent 24 to move away from the latter allowing the latch 32 to swing backwards and away from the adjoining side wall of the body 10, with corresponding flexure of the arm 33 of the detent away from said side part. The leg 32A, engaging the opposing surface of the detent 24, has the function of forcing detent 24 upwards (as viewed in FIG. 6) as the latch 32 swings backwards, thereby to assist in disengaging the abutment face of the detent 24 from the opposing abutment face of the latch 32. Of course, after fracture of the connection 42 in the manner described, the latch arrangement cannot be used to hold the back plate 12 in a fully closed position relative to the body part, thus ensuring that the centrifugation device is a single use device.

The invention claimed is:

1. A centrifugation device comprising a combined sample chamber and slide holder adapted to be mounted, with a microscope slide, in a centrifuge in a predetermined position, after placing, in the sample chamber, a fluid biological sample containing cells, the centrifugation device comprising an integrally moulded body affording a base adapted for engagement with a microscope slide, structure on one side of the base defining a chamber for a fluid sample, with an opening for the introduction of fluid to said chamber, the base including an aperture and carrying a means for sealing the edges of such aperture with respect to the surface of a microscope slide placed across the base, or for allowing the passage of liquid but obstructing the passage of cells, the centrifugation device further including a back plate connected with the base plate by an integral hinge and a latch mechanism formed integrally with the remainder of the device and arranged, when the back plate is closed against the rear of a microscope slide engaged with the base, to locate the slide between the base and the back plate and to hold the back plate in this closed position until fracture of a retaining element from the integrally moulded body;

wherein the latch mechanism comprises a back plate detent carried by the back plate adjacent a free edge of the latter and which, in operation, co-operates in the closed position of the device, with a complementary latch carried by the body of the device and connected with said body by an integral live hinge, the latch mechanism further comprising a shield element which in the condition of the device before use, is secured in a position in which it extends over the complementary latch at a predetermined distance from the integral live hinge of the complementary latch, the arrangement being such that in the closed position, with the shield element still attached, the back plate detent is retained between the shield element and the complementary latch and the shield element counteracts a turning moment applied to the complementary latch as a result of tension in the back plate detent, whilst on breaking of a frangible retaining element holding the shield member in position relative to the device body, the shield element is able to move away from the complementary latch allowing the latter to swing away from the back plate detent for release of the back plate detent to allow the back plate to swing away from the body of the device and to allow removal of the microscope slide.

2. A centrifugation device according to claim 1, wherein said complementary latch is provided with a retaining arm which engages a face of said back plate detent to push the detent across the abutment face of the latch as the latch tilts outwardly and backwards during the release of the detent after rupture of the connection of the shield element with the body part, and thus to ensure release of the back plate detent from the latch.

3. A centrifugation device according to claim 2, wherein said shield element is in the form of a lever which is pivotally connected with said body of the centrifugation device for pivoting about an axis generally perpendicular to the pivotal axis of the back plate with respect to said body defined by said integral hinge and generally perpendicular to the direction of movement of said detent as it moves into engagement with said complementary latch, and wherein said frangible retaining element normally holds said lever against pivoting but, once fractured, allows said lever to pivot about its pivotal axis to move the part of said lever adjacent said latch away from said latch.

4. A centrifugation device according to claim 3, wherein the pivotal connection of said lever with said body is also provided by a living integral hinge.

5. A centrifugation device according to claim 3 or claim 4, wherein said pivotal connection is intermediate opposite ends of said lever, said frangible connection is at one of said ends of said lever and said latch is located between said frangible connection and said pivotal connection, and wherein the other of said end of said lever is free, whereby said frangible connection can be broken by pressing said other of said two ends of said lever toward said body portion, to swing said one end and the region of the lever between said one end and said pivotal connection, away from said latch.

6. A centrifugation device comprising a combined sample chamber and slide holder adapted to be mounted, with a microscope slide, in a centrifuge in a predetermined position, after placing, in the sample chamber, a fluid biological sample containing cells, the centrifugation device comprising an integrally moulded body affording a base adapted for engagement with a microscope slide, structure on one side of the base defining a chamber for a fluid sample, with an opening for the introduction of fluid to said chamber, the base including an aperture and carrying a means for sealing the edges of such aperture with respect to the surface of a microscope slide placed across the base, or for allowing the passage of liquid but obstructing the passage of cells, the centrifugation device further including a back plate connected with the base plate by an integral hinge and a latch mechanism formed integrally with the remainder of the device and arranged when the back plate is closed against the rear of a microscope slide engaged with the base, to locate the slide between the base and the back plate and to hold the back plate in this closed position until fracture of a retaining element from the integrally moulded body;

wherein the latch mechanism comprises a back plate detent carried by the back plate adjacent a free edge of the latter and which, in operation, co-operates in the closed position of the device, with a complementary latch carried by the body of the device and connected with said body by an integral live hinge the latch mechanism further comprising a shield element which, in the condition of the device before use, is secured in a position in which it extends over the complementary latch at a predetermined distance from the integral live hinge of the complementary latch, the arrangement being such that in the closed position with the shield element still attached, the back plate detent is retained between the shield element and the complementary latch and the shield element counteracts a turning moment applied to the complementary latch as a result of tension in the back plate detent, whilst on breaking of a frangible retaining element holding the shield member in position relative to the device body, the shield element is able to move away from said complementary latch allowing the latter to swing away from the back plate detent for release of the back plate detent to allow the back plate to swing away from the body of the device, and to allow removal of the microscope slide;

wherein said means for sealing the edges of said aperture comprises an elastomeric gasket carried by said base and encircling said aperture, for engagement with such microscope slide placed across said base.

7. A centrifugation device according to claim 6, wherein said elastomer is an injection moulded elastomer and is moulded in situ with said body in a two-shot moulding process in which said body and back plate are formed in one moulding shot and the gasket is formed in the other moulding shot.

8. A centrifugation device according claim 6 or claim 7 in which the material of said gasket includes an oil component which, in use, forms an oil film on the microscopic slide where the gasket contacts the slide, which soon act as a barrier to aqueous fluid and thus tends to prevent migration of such fluid past the region of the slides contacted by the gasket, after opening of the centrifugation device and removal of the slide.

* * * * *